(12) United States Patent
Spenciner

(10) Patent No.: US 12,070,199 B2
(45) Date of Patent: *Aug. 27, 2024

(54) SURGICAL INSTRUMENT FOR GRAFT HARVESTING

(71) Applicant: Medos International Sarl, Le Locle (CH)

(72) Inventor: David B. Spenciner, North Attleboro, MA (US)

(73) Assignee: Medos International Sarl, Le Locle (CH)

( * ) Notice: Subject to any disclaimer, the term of this patent is extended or adjusted under 35 U.S.C. 154(b) by 269 days.

This patent is subject to a terminal disclaimer.

(21) Appl. No.: 17/680,545

(22) Filed: Feb. 25, 2022

(65) Prior Publication Data

US 2022/0175354 A1    Jun. 9, 2022

Related U.S. Application Data

(60) Continuation of application No. 16/565,880, filed on Sep. 10, 2019, now Pat. No. 11,291,435, which is a division of application No. 14/731,058, filed on Jun. 4, 2015, now Pat. No. 10,448,935.

(51) Int. Cl.
*A61B 17/00* (2006.01)

(52) U.S. Cl.
CPC ............ *A61B 17/00008* (2013.01); *A61B 2017/00969* (2013.01)

(58) Field of Classification Search
CPC .......... A61B 17/00008; A61B 2017/00969
See application file for complete search history.

(56) References Cited

U.S. PATENT DOCUMENTS

| 5,871,496 A | 2/1999 | Ginn et al. |
| 6,007,495 A * | 12/1999 | Matula .............. A61B 10/0266 |
| | | 600/564 |
| 6,110,190 A | 8/2000 | Ginn et al. |
| 6,328,749 B1 | 12/2001 | Kalmann et al. |
| 7,163,547 B2 | 1/2007 | Majlessi |

(Continued)

OTHER PUBLICATIONS

U.S. Appl. No. 14/731,058, filed Jun. 4, 2015, Surgical Instrument for Graft Harvesting.

(Continued)

*Primary Examiner* — Sarah A Long
(74) *Attorney, Agent, or Firm* — Mintz Levin Cohn Ferris Glovsky and Popeo, P.C.

(57) ABSTRACT

Instruments and methods for harvesting a tissue structure such that a tendon graft are provided. In general, the surgical instrument includes an elongate shaft and an end effector pivotally coupled to a distal end thereof. The end effector defines a tissue seating passage configured to seat therethrough a portion of the tendon when the end effector is in use. The end effector is configured to be manipulated such that either its first or second end is positioned as a leading end. A method for using the end effector to harvest a tendon includes using the end effector to strip and cut the tendon at one end thereof when the first end of the end effector is a leading end, manipulating the end effector such that its second end becomes the leading end, and using the end effector to strip and cut the tendon at another, opposite end thereof.

11 Claims, 8 Drawing Sheets

(56) References Cited

U.S. PATENT DOCUMENTS

| | | | |
|---|---|---|---|
| 7,578,819 B2 | 8/2009 | Bleich et al. | |
| 7,670,338 B2 * | 3/2010 | Albrecht | A61B 18/14 |
| | | | 600/568 |
| 10,448,935 B2 | 10/2019 | Spenciner | |
| 11,291,435 B2 | 4/2022 | Spenciner | |
| 2003/0181907 A1 * | 9/2003 | Lindsay | A61B 18/148 |
| | | | 606/49 |
| 2006/0217697 A1 | 9/2006 | Lau et al. | |
| 2006/0264993 A1 * | 11/2006 | Lee | A61B 17/00008 |
| | | | 606/167 |
| 2006/0276815 A1 | 12/2006 | Lotti et al. | |
| 2008/0161809 A1 | 7/2008 | Schmitz et al. | |
| 2010/0292533 A1 | 11/2010 | Kasahara et al. | |
| 2012/0330339 A1 | 12/2012 | Sengun | |
| 2013/0282009 A1 * | 10/2013 | Knodel | A61B 18/1482 |
| | | | 606/47 |

OTHER PUBLICATIONS

U.S. Appl. No. 16/565,880, filed Sep. 10, 2019, Surgical Instrument for Graft Harvesting.

Austos (Jan. 29, 2014) "AE-FD610R, Assmus Nerve Stripper for Sural Nerve Exision in Autogenous Nerve Grafting, 395 mm, 15 1/2", Austos.com <http://austos.com/tendon-strippers/ae-fo940r-2>, 2 pages.

Prodromos et al. (Oct. 2005) "A Meta-analysis of Stability After Anterior Cruciate Ligament Reconstruction as a Function of Hamstring Versus Patellar Tendon Graft and Fixation Type", Arthroscopy, 21(10):1202.e1-1202.e9.

Yasin et al. (2010) "Accessory Bands of The Hamstring Tendons: A Clinical Anatomical Study", Clinical Anatomy, 23(7):862-865.

* cited by examiner

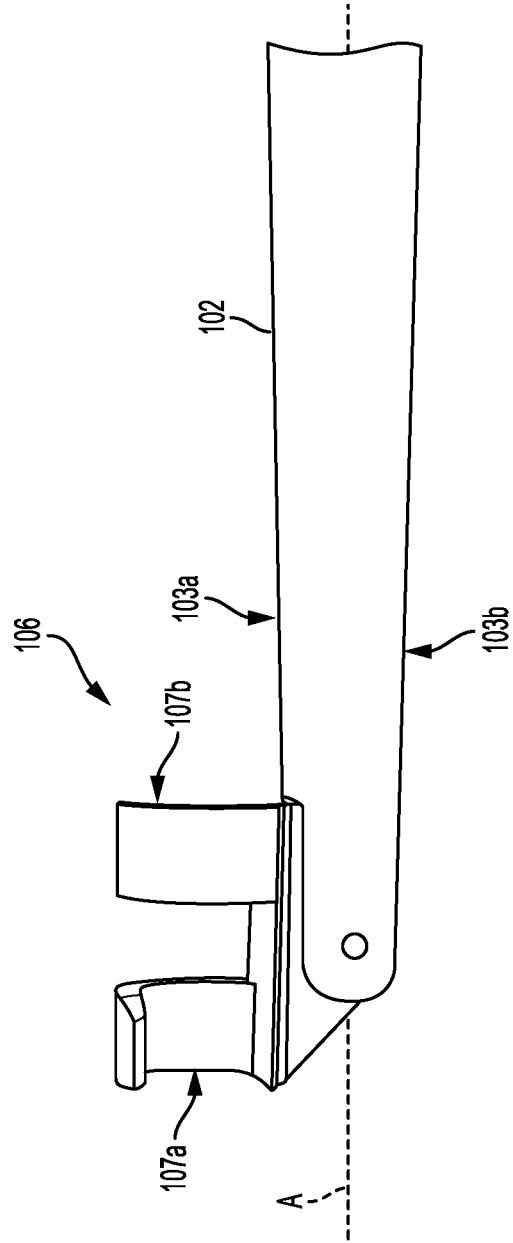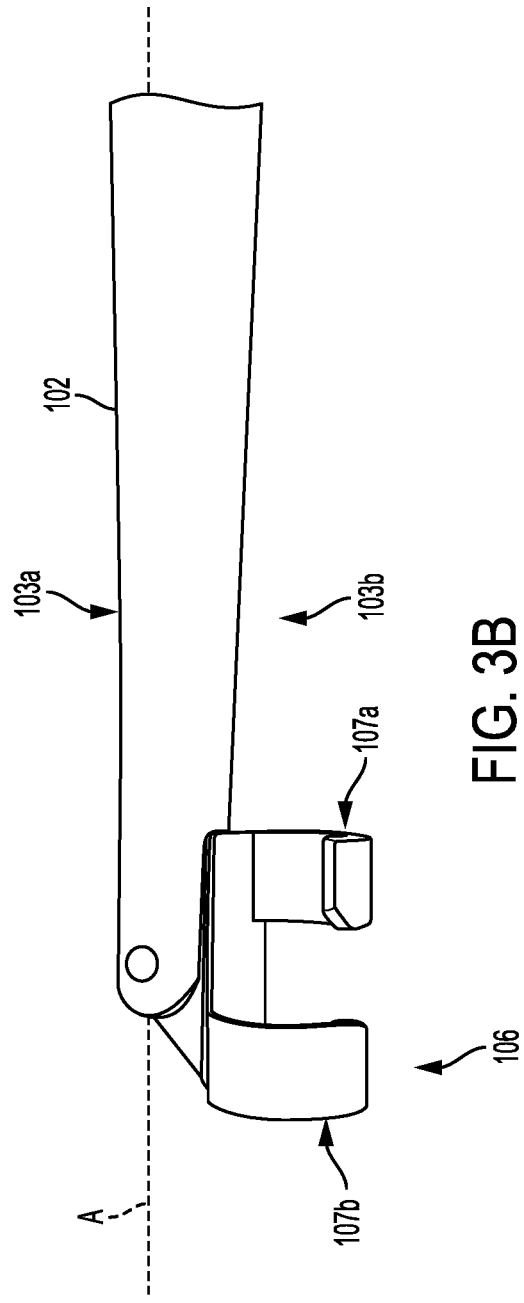
FIG. 3A
FIG. 3B

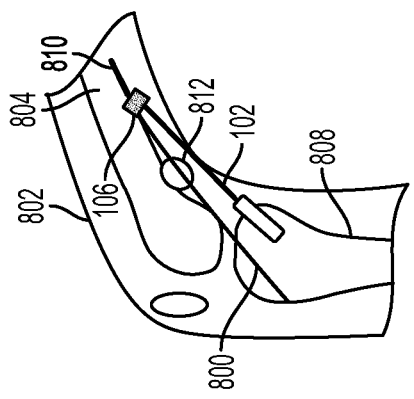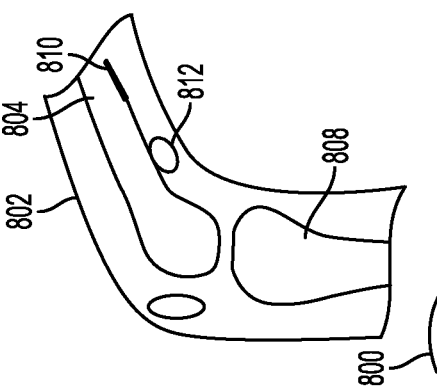
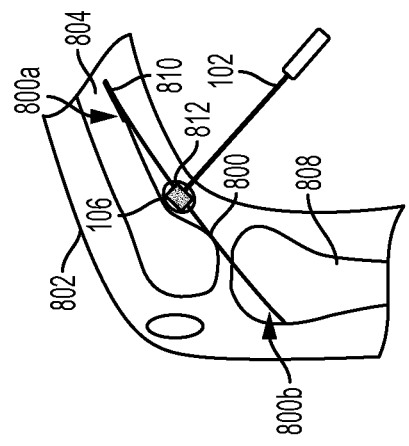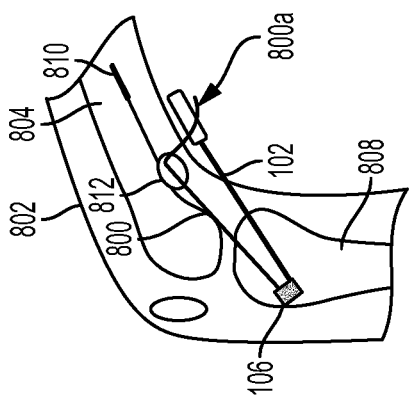
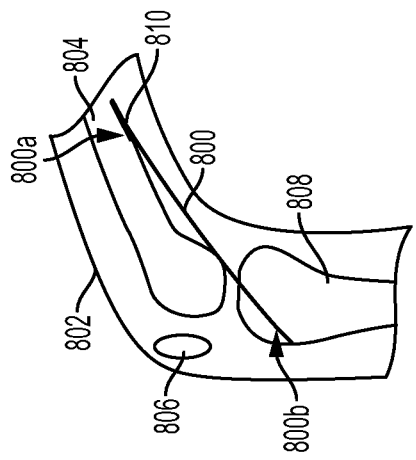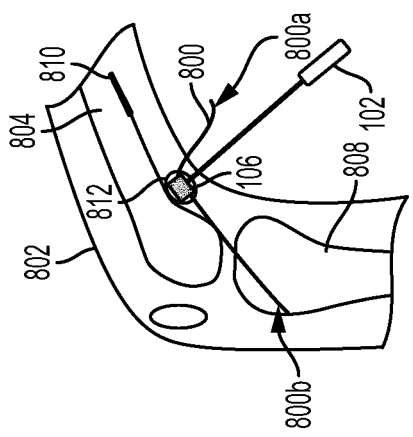

SURGICAL INSTRUMENT FOR GRAFT HARVESTING

CROSS REFERENCE TO RELATED APPLICATIONS

The present application is a continuation of U.S. Ser. No. 16/565,880 entitled "A Surgical Instrument for Graft Harvesting" filed Sep. 10, 2019, which is a divisional of U.S. patent application Ser. No. 14/731,058 (now U.S. Pat. No. 10,448,935) entitled "A Surgical Instrument for Graft Harvesting" filed Jun. 4, 2015, which are hereby incorporated by reference in their entireties.

FIELD

A surgical instrument for graft harvesting as well as methods for using such surgical instrument are provided.

BACKGROUND

A ligament is a piece of fibrous tissue which connects one bone to another within the body. Ligaments are frequently damaged (e.g., detached, torn or ruptured) as the result of injury or accident. A damaged ligament can impede proper stability and motion of a joint and cause significant pain. A damaged ligament can be replaced or repaired using various procedures, a choice of which can depend on the particular ligament to be restored and on the extent of the damage. When ligaments are damaged, surgical reconstruction can be necessary, as the ligaments may not regenerate on their own.

An example of a ligament that is frequently damaged as a result of injury, overexertion, aging and/or accident is the anterior cruciate ligament (ACL) that extends between a top of the tibia and a bottom of the femur. Other ligaments that are often damaged and may need to be replaced include a posterior cruciate ligament (PCL) and medial collateral ligament (MCL). A damaged ACL, PCL, or MCL can cause instability of the knee joint, arthritis, and substantial pain.

ACL reconstruction or repair typically includes the use of a tendon graft replacement procedure which usually involves, for example, drilling a bone tunnel through the tibia and the femur. Then a graft, which may be an artificial ligament or harvested graft, such as a tendon, is secured at the sites where the natural ligament attaches.

Harvesting a tendon graft can be a challenging task that can define the outcome of the ACL reconstruction procedure. A number of conventional procedures exist for harvesting a tendon graft from a donor site. However, many existing approaches have certain shortcomings. For example, a traditional incision for graft harvesting is made anteriorly, at a location in the subject's knee where the semitendinosus and gracilis tendons are not separate tendons, which can complicate identification of the tendons. Furthermore, accessory bands arising from the semitendinosus and gracilis tendons can complicate tendon harvesting by diverting a harvesting instrument such that the main tendon can be cut short at the accessory band level. Such premature amputation of the tendon can result in a graft that is too short to allow adequate ACL reconstruction.

Accordingly, there is a need for improved graft harvesting instruments and techniques for using such instruments.

SUMMARY

A surgical instrument is provided that in some aspects can include an elongate shaft having a longitudinal axis, a proximal end, and a distal end, and an end effector mounted on the distal end of the elongate shaft. The end effector can have first and second ends and it is configured to receive and seat a length of tissue, and it includes a tissue seating passage extending substantially parallel to the longitudinal axis of the shaft in an operative position that is defined at least in part by an arcuate inner wall. The end effector is pivotally mounted on the shaft such that the end effector is configured to be rotatably manipulated during a procedure such that the first end of the end effector can be selectively positioned to be one of a leading end and a trailing end.

The end effector can vary in a number of ways. For example, the end effector can include a tissue retaining portion including the tissue seating passage and a connecting portion coupled to the tissue retaining portion and configured to rotatably couple the end effector to the distal end of the elongate shaft. The distal end of the elongate shaft can have a longitudinal slot configured to rotatably seat therein the connecting portion of the end effector. At least one of the first and second ends of the end effector can have a sharp edge. One of the first and second ends of the end effector can have a sharp protrusion extending beyond at least one member having the arcuate inner wall.

The tissue retaining portion can vary in a number of ways. For example, the tissue retaining portion can include a base portion and longitudinally spaced apart first and second arcuate members extending from and coupled to the base portion at opposite sides of a longitudinal axis of the base portion so as to define the tissue seating passage. The tissue retaining portion can be in the form of a substantially tubular member. The tubular member can have at least one slot formed therein along a length thereof. The at least one slot can be curved.

The surgical instrument can further include a handle coupled to the proximal end of the elongate shaft. In some aspects, the surgical instrument can include at least one locking feature configured to lock the end effector in a first position when the first end thereof is positioned to be the leading end or to lock the end effector in a second position when the second end thereof is positioned to be the leading end.

A surgical instrument is also provided that in some aspects includes an elongate shaft having a longitudinal axis, a proximal end, and a distal end; and a tissue cutting guide pivotally mounted to the distal end of the elongate shaft, the tissue cutting guide being selectively positionable adjacent one of a first side of the shaft and an opposed second side of the shaft, wherein a first end of the tissue cutting guide is a leading end of the tissue cutting guide when it is positioned adjacent the first side of the shaft and wherein the first end of the tissue cutting guide is a trailing end of the tissue cutting guide when it is positioned adjacent the second side of the shaft.

The tissue cutting guide can vary in a number of ways. For example, the tissue cutting guide can include a tissue retaining portion defining a tissue seating passage, and a connecting portion coupled to the tissue retaining portion and configured to pivotally couple the tissue cutting guide to the distal end of the elongate shaft. The tissue retaining portion can include two spaced apart arcuate arms extending from opposite ends of the connecting portion, the arcuate arms being curved in opposite circumferential directions along a length of the connecting portion. The tissue retaining portion can be in the form of a substantially cylindrical elongate member.

A method of harvesting a tissue structure is also provided that in some aspects includes inserting a surgical instrument including an elongate shaft and an end effector coupled to a distal end of the elongate shaft into an incision adjacent a mid-point of the tissue structure, the end effector having first and second ends and being pivotally mounted on the shaft to be rotatably manipulated such that the first end of the end effector can be selectively positioned to be one of a leading end and a trailing end. The method also includes coupling the end effector to the tissue structure near the mid-point thereof such that a portion of the tissue structure extends through a tissue seating passage defined by the end effector; with the first end positioned to be the leading end, the second end positioned to be the trailing end, and the end effector coupled to the tissue structure, advancing the end effector along the tissue structure from the mid-point towards a first end of the tissue structure; and stripping and cutting the tissue structure at the first end thereof. The method further includes, after the tissue structure is cut at the first end thereof, returning the end effector coupled to the tissue structure to a location near the incision; manipulating the end effector such that the second end thereof is positioned to be the leading end, and the first end thereof is positioned to be the trailing end; with the second end of the end effector positioned to be the leading end, the first end of the end effector positioned to be the trailing end, and the end effector coupled to the tissue structure, advancing the end effector along the tissue structure from the location near the incision towards an opposite, second end of the tissue structure; and stripping and cutting the tissue structure at the second end thereof.

The method can vary in a number of ways. For example, the method can further include, after the tissue structure is cut at the first end thereof, withdrawing the first end of the tissue structure from the incision. The inserting step can be conducted through a posterior incision. The tissue structure is at least one of the gracilis tendon and semitendinosus tendon. The first end of the tissue structure can be a proximal end, and the second end of the tissue structure can be a distal end.

In some aspects, after the tissue structure is cut at the first end thereof, the end effector coupled to the tissue structure is returned to the location near the incision without removing the end effector from within the incision. Manipulating the end effector can include pivotally rotating the end effector with respect to the shaft. The tissue structure can be a tendon, nerve or vein.

BRIEF DESCRIPTION OF THE DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings:

FIG. 3A is a side view of the distal end of the surgical device of FIG. 1A showing an end effector having a first end positioned to be a leading end;

FIG. 3B is a side view of the distal end of the surgical device of FIG. 3A showing the end effector having a second end positioned to be a leading end;

FIGS. 8A-8F are schematic illustrations of one embodiment of a method of harvesting a tendon using a described surgical instrument.

DETAILED DESCRIPTION

Figure 1A:
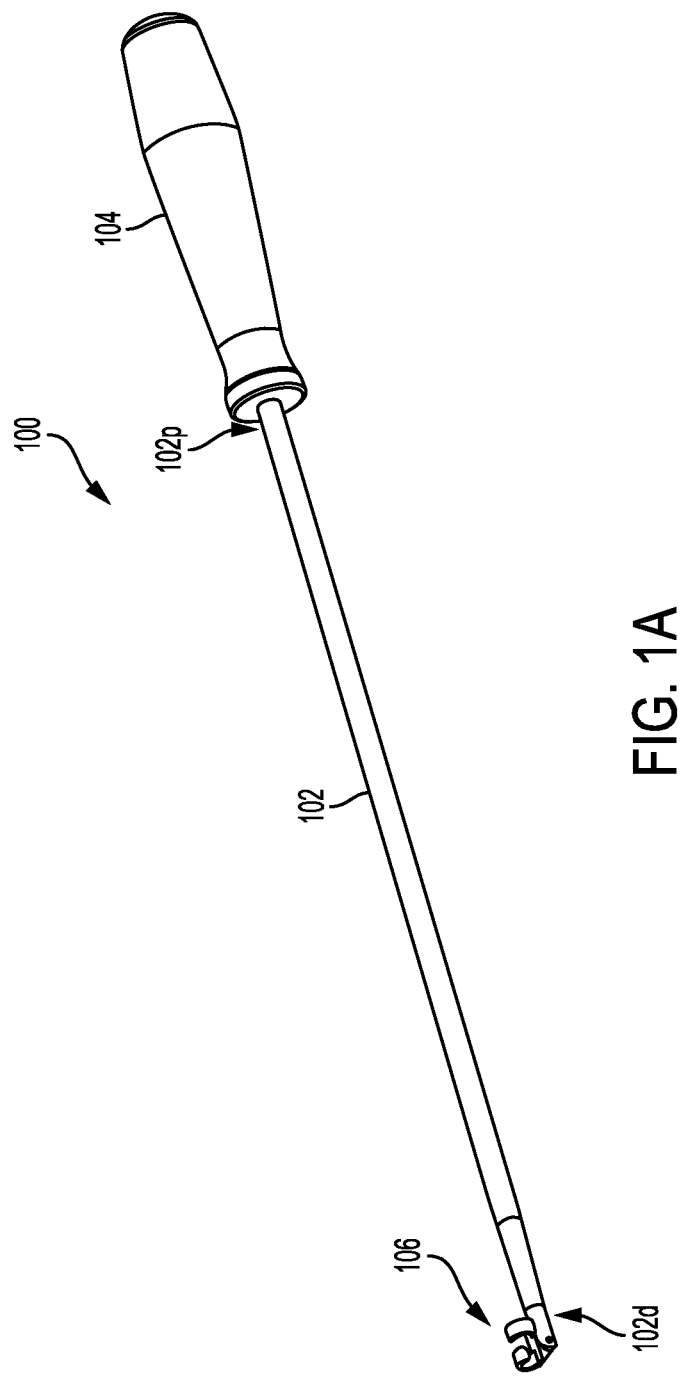
FIG. 1A is a perspective view of one embodiment of a surgical device.

Certain exemplary embodiments will now be described to provide an overall understanding of the principles of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the embodiments is defined solely by the claims. Further, the features illustrated or described in connection with one exemplary embodiment may be combined with the features of other embodiments. Such modifications and variations are intended to be included within the scope of the described embodiments.

The embodiments described herein generally relate to instruments and methods for harvesting tendon grafts for ligament reconstruction or augmentation surgeries. However, the described techniques can also be used for harvesting other anatomical structures, such as, for example, nerves and veins. A surgical instrument is provided that includes an elongate shaft and an end effector pivotally mounted on a distal end of the shaft. The end effector defines a tissue seating passage extending between first and second ends thereof and configured to receive a portion of the tendon when the surgical instrument is in use. The end effector can be rotatably manipulated to be positioned at multiple angles with respect to a longitudinal axis of the elongate shaft while the tendon remains associated with the tissue seating passage. In an operative position, the end effector can be positioned such that the tissue seating passage is substantially parallel to the longitudinal axis of the elongate shaft and one of the first and second ends of the end effector is selectively positioned as a leading or trailing end of the end effector. The leading end is used to strip and cut the tendon. Thus, the end effector allows one to strip and to cut both ends of the tendon by positioning either the first or second end of the end effector as a leading end. In some aspects, the first and second ends can have a configuration that facilitates harvesting a tendon at a location having certain anatomical characteristics.

A method of harvesting a tendon including using a surgical instrument as described herein is also provided. The method involves making an incision adjacent a mid-point of the tendon and coupling the surgical instrument to the tendon. In the illustrated embodiments, the incision is a posterior incision made on the back of a patient's knee. The posterior incision facilitates easy identification of a tendon, such as the semitendinosus or gracilis tendon, because at that location these tendons are present as separate tendons.

A first end of the end effector of the surgical instrument can be positioned as a leading end whereas a second end of the end effector is a trailing end. The effector is then advanced along the tendon from the mid-point towards a first end of the tendon to then strip and cut the tendon at its first end. After the tendon is cut at its first end, the surgical instrument is brought back to a location near the incision and the end effector is manipulated (e.g., rotated with respect to an elongate shaft of the instrument) such that the second end of the end effector becomes a leading end while the first end is now positioned as a trailing end. The end effector, which remains coupled to the tendon, can then be advanced from the mid-point towards a second end of the tendon to then strip and cut the tendon at its second end.

The instruments and methods described herein provide a number of advantages over existing techniques for harvesting tendons. For example, the described techniques reduce a risk of premature amputation of the tendon. This increases a possibility of a success of the procedure and decreases a chance of unnecessary damage to a tendon and trauma to the patient. Also, patient satisfaction can be improved since the incision is located on the back of the patient's knee and is thus less visible. Furthermore, the described surgical instrument enables harvesting a tendon at its both ends while the instrument remains associated with the tendon. Because the posterior incision is made to access a tendon, the surgical instrument can have a smaller length as compared to conventional stripping instruments, which facilitates operation of the surgical instrument. In addition, the first and second ends of the end effector of the surgical instrument can be configured to facilitate graft harvesting at specific anatomical locations when the ends are used as leading ends.

The described instruments and methods can be used in conjunction with harvesting various tendons, such as the gracilis and semitendinosus tendons, which can then be used in a variety of different surgical contexts. Furthermore, harvested tendon grafts can be utilized in connection with surgical procedures for repairing or replacing ligaments in a variety of joints. In some embodiments, tendon grafts harvested as described herein have particular utility in cruciate ligament reconstruction procedures such as, for example, the cruciate ligaments of the knee.

FIGS. 1A, 1B and 2A-2C illustrate one example of a surgical instrument 100 for harvesting a tendon. The surgical instrument 100 includes a tissue cutting guide or an elongate shaft 102 having proximal and distal ends 102p, 102d and a longitudinal axis A extending therethrough. As shown in FIG. 1A, the elongate shaft 102 can be coupled at the proximal end 102p thereof to a handle 104 configured to hold and manipulate the surgical instrument 100. The surgical device 100 also includes an end effector 106 pivotally mounted on the distal end 102d of the elongate shaft 102. The surgical instrument 100 can be formed from any suitable material, for example, a metal or polymer.

Figure 1B:
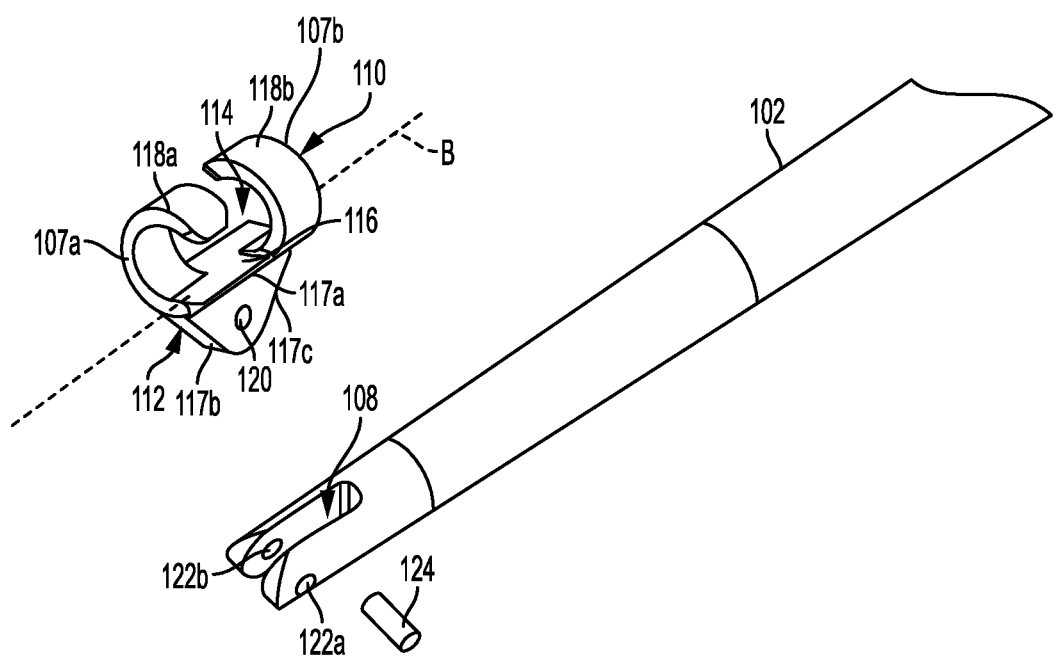
FIG. 1B is a perspective exploded view of a distal end of the surgical device of FIG. 1A.

As shown, the elongate shaft 102 is a generally cylindrical element having the handle 104 coupled proximally thereto. The outer surface of the elongate shaft 102 can be generally smooth and the elongate shaft 102 or a portion, such as a distal portion, thereof can be distally tapered to facilitate insertion of the instrument 100 into an incision in a subject's body. As shown in FIG. 1B, the distal end 102d of the elongate shaft 102 has a longitudinal slot 108 configured to pivotally seat therein the end effector 106, as discussed in more detail below. The elongate shaft 102 can have any suitable dimensions. For example, a length of the elongate shaft 102 can range from about 20 cm to about 30 cm. In one aspect, the length of the elongate shaft 102 can be about 28 cm. A diameter of the elongate shaft 102 can range from about 3 mm to about 7 mm. In one aspect, the diameter of the elongate shaft 102 at its distal end 102d can be about 4 mm. However, a person skilled in the art will understand that the elongate shaft 102 can have other dimensions.

The handle 104 can have a variety of configurations and sizes, as the described embodiments are not limited in this respect. The handle 104 can have suitable features that facilitate grip such that the handle 104 can be conveniently used to hold and operate the surgical instrument 100. In some aspects, a length of the handle can range from about 10 cm to about 20 cm. In one aspect, the length of the handle 104 can be about 11 cm.

Figure 2A:
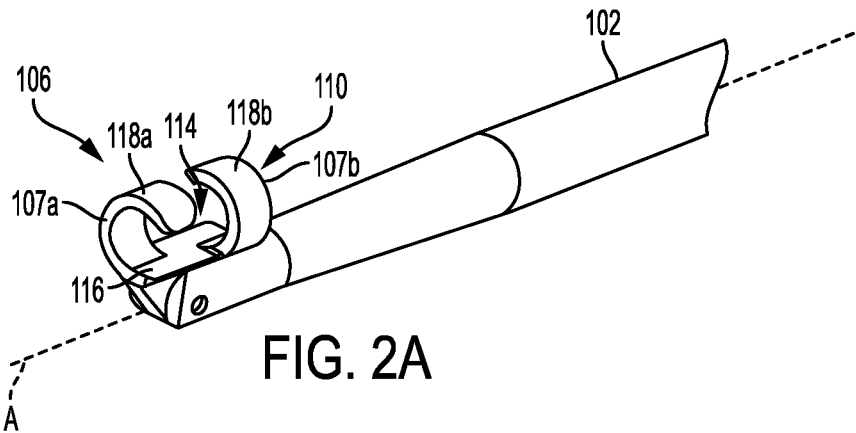
FIG. 2A is a perspective view of a distal end of the surgical device of FIG. 1A.
Figure 2B:
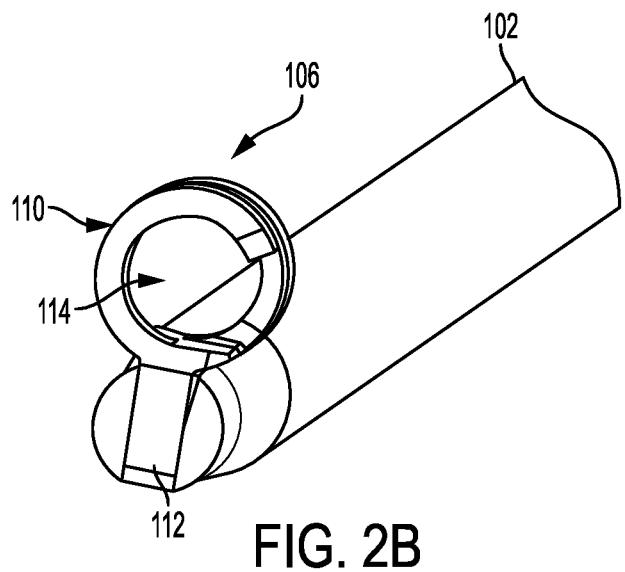
FIG. 2B is a front perspective view of the distal end of the surgical device of FIG. 1A.
Figure 2C:
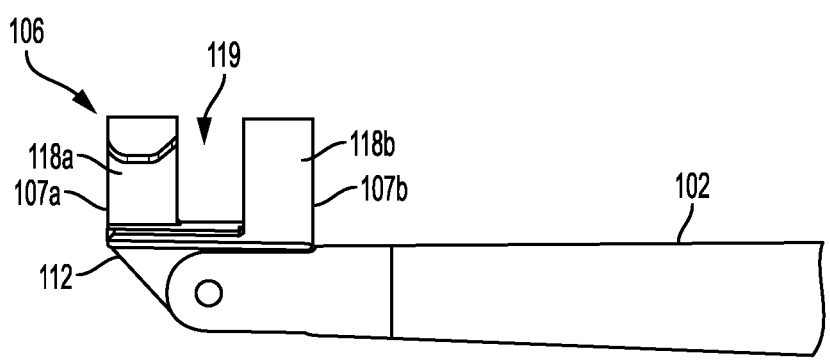
FIG. 2C is a side view of the distal end of the surgical device of FIG. 1A.

As shown in FIGS. 1B, 2A and 2B, the end effector 106 includes a tissue retaining portion 110 and a connecting portion 112 coupled to the tissue retaining portion 110 and configured to rotatably couple the end effector 106 to the distal end 102d of the elongate shaft 102.

The tissue retaining portion 110 can have a variety of configurations. In the illustrated embodiment, the tissue retaining portion 110 is generally cylindrical and has a base portion 116 and longitudinally spaced apart first and second arcuate members 118a, 118b extending from and coupled to the base portion 116 at opposite sides of a longitudinal axis B (FIG. 1B) of the base portion 116. The first and second arcuate members 118a, 118b are curved towards one another in a "pig-tail" configuration so as to define a tissue seating passage 114 defined at least in part by arcuate inner walls of the first and second arcuate members 118a, 118b. The tissue seating passage 114 extends substantially parallel to the longitudinal axis A of the elongate shaft 102 in an operative position, as described in more detail below. The tissue seating passage 114 is configured to receive a portion of the tendon extending therethrough when the surgical instrument 100 is in use. As shown in FIG. 2B, the first and second arcuate members 118a, 118b are coupled to the base portion 116 such that their inner arcuate walls defining the tissue seating passage 114 are aligned along the base portion 116. In the illustrated embodiment, the tissue seating passage 114 has a round or oval cross-sectional shape. However, the tissue seating passage can have other configurations and various cross-sectional shapes. For example, in some aspects, the tissue retaining portion can include more than two arcuate members extending from and coupled to the base portion. Furthermore, some or all of the arcuate members can be coupled at the same side of the base portion.

The outer side walls of the first and second arcuate members 118a, 118b define first and second ends 107a, 107b of the end effector 106. The first and second ends 107a, 107b have a shape that is based on a configuration of the end effector. Thus, in the illustrated example, the first and second ends 107a, 107b are shaped as arcuate outer side walls of the end effector 106.

The end effector 106 can pivot with respect to the elongate shaft 102 such that each of the first and second ends 107a, 107b can be selectively positioned to be a leading or trailing end, depending on an orientation of the end effector 106 with respect to the shaft 102. For example, when the end effector 106 is positioned adjacent to one side of the elongate shaft 102 as shown in FIGS. 1A, 1B, and 2A-2C, the first end 107a is positioned as the leading or forward end of the surgical device 100 whereas the second end 107b is positioned as the trailing end.

As shown in FIGS. 1A, 1B, 2A and 2C, the first and second arcuate members 118a, 118b are longitudinally spaced apart such that a slot or gap 119 (FIG. 2C) is formed therebetween. The gap 119 can have a width selected so as to facilitate coupling a tendon with the end effector 106. For example, in some aspects, the gap 119 can range from about 2 mm to about 7 mm. In one example, the gap 119 can be about 5 mm. Furthermore, it should be appreciated that the end effector can be configured to have a slot or gap having other configurations that facilitate coupling the end effector to a tendon. For example, the slot of a suitable width can be a spiral slot or a slot having any other shape. The slot can extend approximately along a length of the end effector.

Referring back to FIG. 1B, the end effector 106 includes the connecting portion 112 that is coupled to the tissue retaining portion 110 and that can have various configurations. In the illustrated example, the connecting portion 112 extends downward from the base portion 116 of the tissue retaining portion 110. The connecting portion 112 can be integrally or monolithically formed with the base portion 116 or it can be a separate component coupled (e.g., welded) to the base portion 116 in a suitable manner. The connecting portion 112 is configured to pivotably fit within the longitudinal slot 108 extending through the distal end 102d of the elongate shaft 102. The slot 108 is formed such that, when the end effector 106 is inserted therein, the connecting portion 112 can pivotally rotate relative to the longitudinal axis A of the elongate shaft 102 such that the first end 107a of the end effector 106 can be selectively positioned to be one of a leading end and a trailing end.

In the illustrated example, the connecting portion 112 is generally triangular-shaped and approximately resembles an isosceles triangle with a longer base edge 117a coupled to the base portion 116 and two other edges 117b, 117c having an equal length, shorter than that of the base edge 117a, extending from the base portion 116 towards the end effector 106. However, a person skilled in the art will appreciate that the connecting portion 112 can have other configurations. For example, the connecting portion can be shaped as equilateral triangle, it can be rectangular, or it can have any other shape.

As shown in FIG. 1B, the connecting portion 112 includes an opening 120 extending therethrough that is disposed approximately mid-way between the edges 117b, 117c. The connecting portion 112 is configured to fit within the longitudinal slot 108 such that the opening 120 is aligned with openings 122a, 122b formed in opposed walls of the distal end 102d of the elongate shaft 102 separated by the slot 108. The openings 122a, 122b at the distal end 102d and the opening 120 within the connecting portion 112 can receive a pin 124 therethrough that thus pivotally couples the connecting portion 112 of the effector 106 to the elongate shaft 102. A person skilled in the art will appreciate that other mechanisms can be used to rotatably couple the effector 106 to the elongate shaft 102, as described embodiments are not limited in this respect. For example, the mechanisms can include a variety of hinges, ball-and-socket joints and any other mechanisms.

Although in the illustrated examples, the end effector 106 is configured to rotate within a single plane as permitted by the configuration of the slot 108, in other aspects, the end effector can be positioned at multiple planes with respect to the elongate shaft (e.g., when a coupling such as a ball-and-socket joint is used). Furthermore, the surgical instrument in accordance with the description here can include a locking mechanism configured to releasably retain the end effector in a certain orientation with respect to the elongate shaft. As another variation, the end effector can be configured and coupled to the elongate shaft such that the end effector can be positioned at different angles with respect to opposite sides of the elongate shaft. In other words, the end effector can be "biased" towards one of the sides of the elongate shaft.

The end effector 106 can have any suitable dimensions. For example, in some aspects, the overall length of the end effector 106 can range from about 3 mm to about 25 mm. In some in some aspects, the length of the end effector 106 can range from about 10 mm to about 15 mm. In one aspect, the length of the end effector 106 can be about 11 mm. A diameter of the end effector 106 can range from about 3 mm to about 7 mm. In one aspect, the diameter of the end effector 106 is about 4 mm. However, a person skilled in the art will understand that the end effector 106 can have other dimensions. Furthermore, the end effector can have irregular shapes, such as oval, bowtie-shaped, bean-shaped, kidney-shaped, or other shapes, in which cases a size of the end effector will vary depending on an intended size of an incision, patient's characteristic and other factors.

As mentioned above, the end effector 106 is pivotally mounted on the elongate shaft 102 such that the end effector 106 can be rotatably manipulated during a graft harvesting procedure. The tissue seating passage 114 of the end effector 106 can receive therein a portion of a tendon being harvested and the end effector 106 can be manipulated to allow either of its ends to be a leading end. As shown in FIGS. 3A and 3B, the end effector 106 can be manipulated such that its first end 107a is selectively positioned to a leading end or a trailing end. In the illustrated examples, the end effector 106 is configured to rotate approximately 180 degrees with respect to the longitudinal axes A of the elongate shaft 102.

Thus, FIG. 3A shows that, when the end effector 106 extends substantially parallel to the longitudinal axis A of the elongate shaft 102 adjacent a first side 103a of the shaft 102, the first end 107a of the end effector 106 is positioned as a leading end. Thus, in such configuration, the first end 107a of the end effector 106 can be used to strip a tendon from the surrounding muscle and other soft tissue and then cut the tendon at a first end thereof. For example, the first end 107a of the end effector 106 can be used to strip and cut a proximal end of the tendon. However, as shown in FIG. 3B, when the end effector 106 is pivoted with respect to the elongate shaft 102 such that the end effector 106 extends substantially parallel to the longitudinal axis A of the elongate shaft 102 adjacent a second, opposite side 103b thereof, the first end 107a is positioned as a trailing end and the second end 107b is positioned as a leading end. When used as the leading end, the second end 107b can be used to strip and cut the tendon at a second, opposite end of the tendon. For example, second end 107b of the end effector 106 can be used to strip and cut a distal end of the tendon. However, a person skilled in the art will appreciate that, depending on a configuration of the end effector, either end of the end effector can be used to strip and cut either end of the tendon.

Figure 3C:
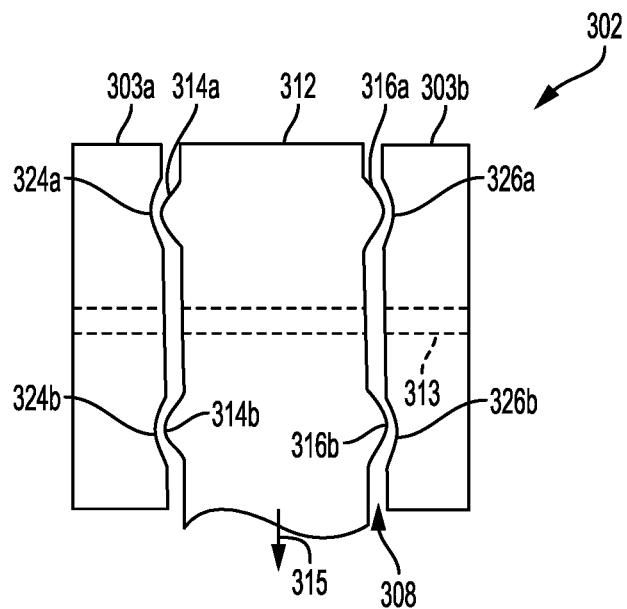
FIG. 3C is a cross-sectional view of a distal end of an elongate shaft of a surgical instrument and a connecting portion of an end effector of the surgical instrument configured to be coupled to one another via a locking mechanism.
Figure 3D:
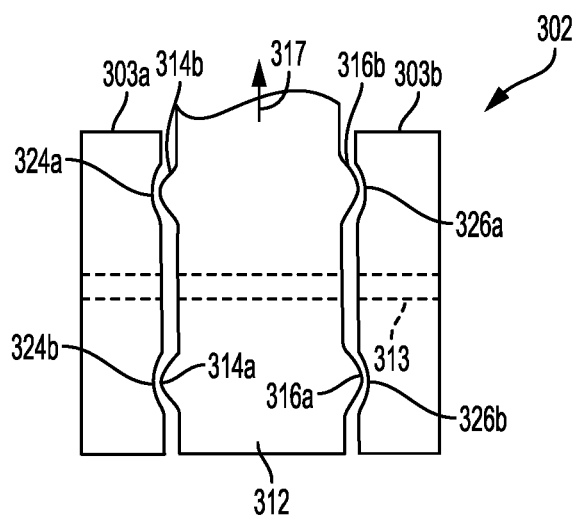
FIG. 3D is another cross-sectional view of the distal end of the elongate shaft and the connecting portion of FIG. 3C.

In some implementations of the current techniques, the surgical instrument can be configured such that a position of the end effector with respect to the elongate shaft can be reversibly locked. For example, the surgical instrument can have one or more locking features that allow the end effector to be locked in a first position when it extends along one side of the elongate shaft such that a first end of the end effector is positioned as a leading end. The end effector can alternatively be locked or secured in a second position when it extends along another, opposite side of the elongate shaft such that a second end of the end effector is positioned as a leading end. FIGS. 3C and 3D illustrate an example of such locking mechanism. FIGS. 3C and 3D show a cross-section of a distal end of an elongate shaft 302 (e.g., elongate shaft 102) of a surgical instrument having a connecting portion 312 disposed within a longitudinal slot 308 configured to pivotally seat therein an end effector of the surgical instrument (not shown). The connecting portion 312 can be similar to connecting portion 112 (e.g., FIGS. 1B and 2C) that extends downward from a base portion of a tissue retaining portion defined by the end effector. Dashed lines 313 illustrate a location of a through passage configured to receive a pin or other connecting element (e.g., pin 124 in FIG. 1B).

As shown in FIG. 3C, the slot 308 separates the distal end of the shaft 302 into first and second arms 303a, 303b. In this example, the locking mechanism can include rounded ridges or protrusions 314a, 314b formed on opposite ends of one side of the connecting portion 312 and rounded ridges or protrusions 316a, 316b formed on opposite ends of another, opposite side of the connecting portion 312. The protrusions 314a, 314b are configured to lockingly mate with respective grooves or recesses 324a, 324b formed on the inner surface of the first arm 303a. Similarly, the protrusions 316a, 316b are configured to lockingly mate with respective grooves or recesses 326a, 326b formed on the inner surfaces of the second arm 303b. The protrusions can be configured to fittedly mate with the respective recesses such that a force is required to be applied to both engage and disengage the protrusions and the recesses. It should be appreciated that the protrusions and recesses are shown by way of example only, as any suitable number of any other features can be used to lock or secure a position of an end effector with respect to the elongate shaft.

In the example of FIG. 3B, it is schematically indicated by an arrow 315 indicated that the end effector is shown to be disposed below the elongate shaft 302. It should be appreciated, however, that the position of the end effector "below" the shaft 302 is shown for illustration purposes only, to demonstrate a position when the end effector is disposed along one end of the elongate shaft such that the end effector is locked at that position by engaging the protrusions 314a, 314b, 316a, 316b on the connecting portion 312 with the recesses 324a, 324b, 326a, 326b on the distal end of the shaft 302. The end effector can then be manipulated so as to disengage the protrusions from the respective recesses and position the end effector along an opposite side of the shaft 302. Thus, as shown by an arrow 317 in FIG. 3D, the effector can be disposed above the elongate shaft 302. The protrusions can then be again engaged with the recesses to lock the position of the end effector with respect to the shaft 302. As shown in FIG. 3D, the protrusions 314b, 314a engage with the recesses 324a, 324b, respectively. The protrusions 316b, 316a engage with the recesses 326a, 326b, respectively, as also shown in FIG. 3D.

As mentioned above, an end effector of a surgical instrument described herein can have a variety of configurations.

Figure 4A:
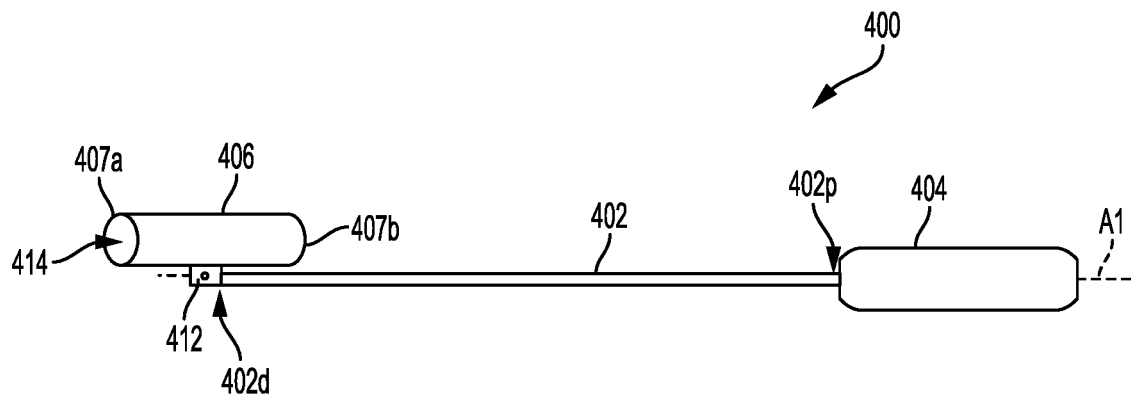
FIG. 4A is a side view of another embodiment of a surgical device showing an end effector having a first end positioned to be a leading end.
Figure 4B:
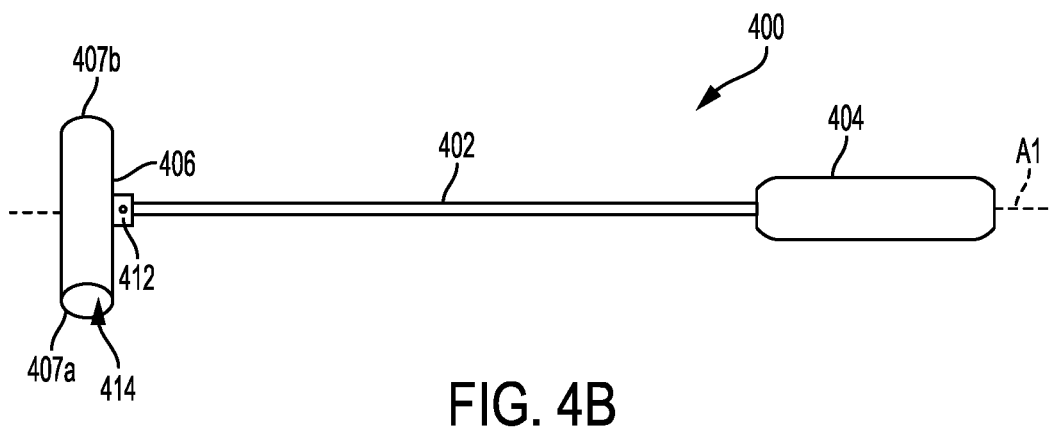
FIG. 4B is a side view of the surgical device of FIG. 4A showing the end effector positioned such that a tissue seating passage extending therethrough is approximately perpendicular to a longitudinal axis of the surgical device.
Figure 4C:
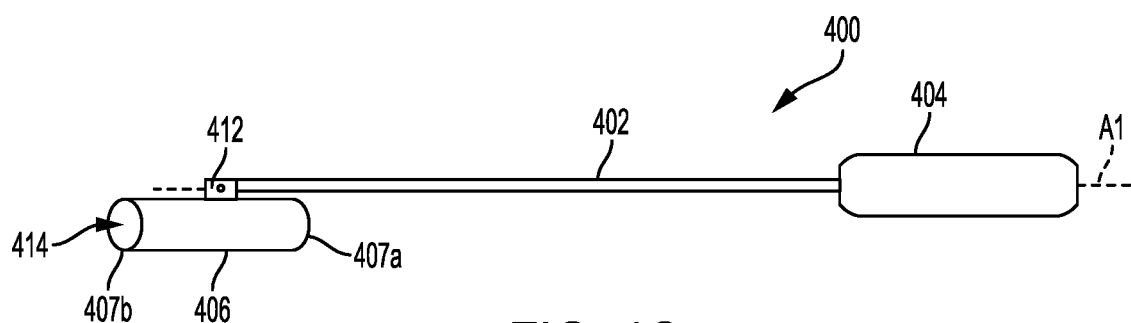
FIG. 4C is a side view of the surgical device of FIG. 4A showing the end effector having a second end positioned to be a leading end.

FIGS. 4A-4C illustrate an example of a surgical instrument 400 having an elongate shaft 402, a handle 404 coupled to a proximal end 402p of the elongate shaft 402, and an end effector 406 pivotally coupled to a distal end 402d of the elongate shaft 402 and having a tubular configuration. As shown in FIGS. 4A-4C, the end effector 406 having first and second ends 407a, 407b has a generally tubular configuration such that inner walls of the end effector 406 define a tissue seating passage 414. In the illustrated example, the outer wall of the end effector 406 does not have a slot formed therein. Thus, when using such an exemplary device, a tendon will be inserted into the end effector 406 to extend through the tissue seating passage 414. In other aspects, an end effector can have a similar tubular configuration and straight or curved slots formed within the outer wall of the end effector (e.g., approximately along a length thereof).

In the example illustrated in FIGS. 4A-4C, the end effector 406 is coupled to the distal end 402d of the elongate shaft 402 using a mechanism similar to that used to couple end effector 106 to elongate shaft 102 (FIGS. 1A, 1B, 2A-2C, 3A and 3B). However, as shown, in this example, a connecting portion 412 of the end effector 406 configured to pivotally mount the end effector 406 on the elongated shaft 402 has a generally rectangular configuration. A person skilled in the art will appreciate, however, that the connecting portion can have any other configurations.

The end effector 406 is configured to be manipulated to be positioned with respect to the elongate shaft 402 such that the first end 407a of the end effector 406 is a leading end (FIG. 4A) or the second end 407b of the end effector 406 is a leading end (FIG. 4C). In the configurations shown in FIGS. 4A and 4C in which the end effector 406 is positioned as ready for tendon harvesting, the end effector 406 is positioned such that the tissue seating passage 414 extends substantially parallel to a longitudinal axis A1 of the elongate shaft 402. FIG. 4B illustrates the end effector 406 in an intermediate position in which the end effector 406 extends substantially perpendicular to the longitudinal axis A1 of the elongate shaft 402, to illustrate that the end effector 406 can be manipulated to be positioned at different angles with respect to elongate shaft 402.

As mentioned above, a tissue seating passage defined by an end effector of a described surgical instrument can have various configurations and cross-sectional shapes. For example, regardless of the specific configuration of the end effector, the tissue seating passage can have a round, oval or other (including irregular) cross-sections. Also, the end effector can have one or more slots or gaps having a variety of configurations defined therein.

Figure 5:
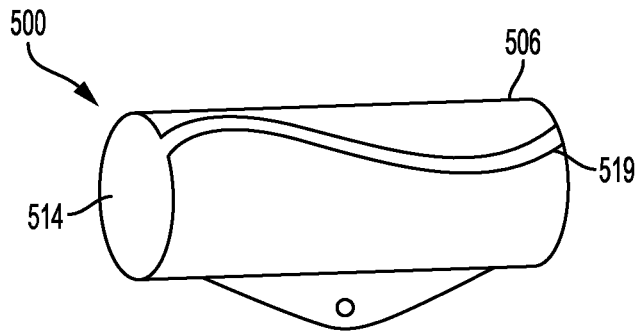
FIG. 5 is a perspective view of one embodiment of an end effector of a surgical instrument.

FIG. 5 illustrates one example of an end effector 506 of a surgical instrument 500 having a curved cut-out or slot 519. The surgical instrument 500 includes other components, such as an elongate shaft having the end effector 506 pivotally mounted thereon, and any other components, which are not shown in FIG. 5. In this example, the end effector 506 is a generally tubular member with its inner walls defining a tissue seating passage 514 extending therethrough. The slot 519 is formed along the length of the end effector 506 and is configured to pass a portion of a tendon therethrough when the surgical instrument 500 is in use. A person skilled in the art will appreciate that the slot 519 can be less or more curved and it can form multiple "waves" along the length of the end effector 506. Furthermore, the slot can be formed such that it winds around opposite sides of the end effector. The curved configuration of the slot 519 can facilitate retaining a portion of the tendon within the tissue seating passage 514 when the surgical instrument 500 is in use.

Figure 6:
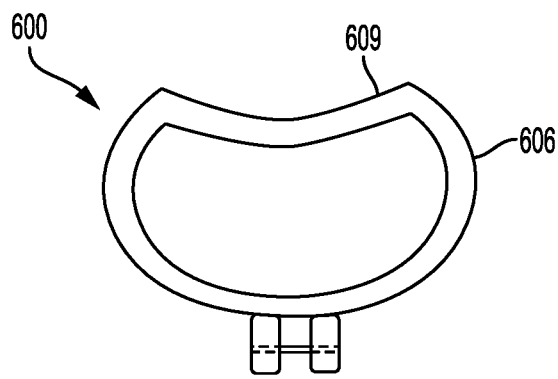
FIG. 6 is an end view of another embodiment of an end effector of a surgical instrument.

FIG. 6 illustrates an example of an end effector 606 of a surgical instrument 600 having a "kidney-like" cross-sectional shape. Specifically, as shown in FIG. 6, a top portion 609 of the end effector 606 is generally concave. Other configurations can be used additionally or alternatively.

As mentioned above, the surgical instrument in accordance with the described aspects is configured such that the first and second ends of the end effector can selectively operate as either a leading or trailing end. Thus, each of the ends of the effector can be configured to be more suitable for stripping and cutting a particular portion of a tendon having certain anatomical specificities. For example, although the first and second ends of the end effector can be either both sharp or both blunt in a uniform manner, in some embodiments, a portion of one or both of the first and second ends can be sharpened and/or shaped in a certain manner depending on characteristics of the portion of the tendon to be harvested using that end.

In some aspects, one or both ends of an end effector of a surgical instrument can have features that facilitate interaction of the instrument with anatomical structures and allow harvesting the graft with a decreased risk of damaging or prematurely amputating the tendon. For example, as known by a person skilled in the art, the accessory bands of the gracilis and semitendinosus tendons separate from a respective main tendon along a similar plane. Thus, an end of the end effector intended to be used to separate and harvest a distal end of a tendon can have features that facilitate this process. This can decrease a possibility of donor site morbidity. Also, using an end effector having ends adapted to anatomical structures within the donor site can decrease or eliminate patient pain which can be caused by harvesting excessive amount of muscle tissue along with the tendon or by pushing a harvesting instrument with an excessive force within the patient's body.

Figure 7:
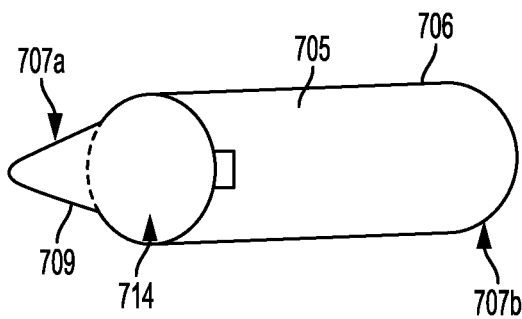
FIG. 7 is a perspective view of one embodiment of an end effector of a surgical instrument.

FIG. 7 illustrates an example of a generally cylindrical hollow end effector 706 having a tissue seating passage 714 extending therethrough. The end effector 706 can have a rounded or oval cross-sectional shape. The first and second ends 707a, 707b of the end effector 706 have different shapes. Specifically, as shown, the first end 707a configured to harvest a tendon at its distal end has an extension 709 extending from one wall of a hollow main body 705 of the end effector 706. Such a configuration can be suitable for deep and superior portions of the gracilis and semitendinosus tendons. In the illustrated example, the extension 709 is generally triangular or V-shaped. However, the extension can have other suitable configurations. Regardless of its specific configuration, the extension 709 can be sharp so as to be used to cut the accessory attachments. The extension 709 will be interfacing with a portion of the tendon where the accessory bands typically arise (superficial and inferior portions). At the same time, the remainder of the outer edge of the first end 707a not occupied by the extension 709 can be blunt, or dull, so as to protect the main trunk of the tendon and to avoid damaging sensitive anatomical structures or prematurely amputating the tendon. Thus, when the end effector 706 is coupled to the tendon such that a portion of the tendon extends through the tissue seating passage 714, and the surgical instrument is moved along the tendon, the accessory bands will be guided by the extension 709 to the point where they are cut.

In the example of the end effector 706 of FIG. 7, the outer edge of the second end 707b that is used to separate and cut the proximal end of the tendon can be uniform, such that it has no surface features and it is blunt or sharp uniformly throughout the outer edge. However, in some aspects, the second end 707b can also have features that facilitate harvesting the tendon at the proximal end thereof.

FIGS. 8A-8F show one example of a method of harvesting a tendon 800 using surgical instrument 100 (FIGS. 1A, 1B, 2A-2C, 3A, and 3B). It should be appreciated that the method is described in connection with the surgical instrument 100 by way of example only, as another surgical instrument that can have any of the end effectors in accordance with the described embodiments can also be used. The tendon 800 can be a hamstring tendon, such as the gracilis or semitendinosus tendon.

FIGS. 8A-8F illustrate medial views of a patient's knee 802 showing a femur 804, a patella 806, a tibia 808, and the tendon 800 to be harvested. The musculotendinous junction 810 of the tendon 800 that remains in the patient after the tendon 800 is harvested is also shown. FIG. 8A shows the knee 802 and the tendon 800 having first (proximal, adjacent to the femur 804) and second (distal, attached to the tibia 808) ends 800a, 800b before the surgical procedure begins. It should be appreciated that the opposite ends of the tendon 800 are identified as the "first" and "second" ends for illustration purposes only, and not to show any particular order. As shown in FIG. 8B, before the surgical instrument 100 is being used, an incision 812 adjacent a mid-point of the tendon 800 is made. In the illustrated embodiment, the incision 812 is a posterior incision made on the back of the patient's knee 802. The incision 812 can be made using any suitable instruments and techniques as known in the art.

After the incision 812 is made, the end effector 106, shown in detail in FIGS. 1A, 1B, 2A-2C, 3A and 3B, and shown only schematically in FIGS. 8B-8E, is inserted into the incision 812 and coupled with the tendon 800. This can be done, for example, by passing a portion of the tendon 800 near the mid-point thereof around the first and second arcuate members 118a, 118b of the end effector 106 (e.g., FIG. 1B) such that the portion of the tendon 800 is seated within and extends through the tissue seating passage 114 defined by the end effector 106. The posterior incision 812 allows proper access to the tendon such that the tendon 800 can be identified relatively easily. For example, a surgeon performing the procedure can identify that the tendon 800 is the gracilis or semitendinosus tendon.

The end effector 106 is positioned with respect to the elongate shaft 102 of the surgical instrument 100 such that the first end 107a thereof is positioned to be a leading end and the second end 107b is positioned as a trailing end, as shown in FIG. 3A. In such a configuration, the end effector 106 is advanced proximally along the tendon 800 from the mid-point towards the first end 800a of the tendon 800, as shown in FIG. 8B. The surgical instrument 100 is operated such that the end effector 106 is advanced proximally towards the musculotendinous junction 810 and the first end 107a (shown in FIG. 3A) operating as the leading end is used to strip the tendon 800 of muscle and other surrounding tissue.

After the end effector 106 is advanced along a sufficient length of the tendon 800, the first end 107a is then used to cut the tendon 800 at the first end 800a thereof near the musculotendinous junction 810. In this way, the first end 800a of the tendon 800 is separated from its attachment point on the muscle adjacent to the femur 804.

After the after the tendon 800 is cut at the first end 800a thereof, the end effector 106, which remains coupled to the tendon 800, is returned to the location near the incision 812, as shown in FIG. 8D. The end effector 106 is advanced distally towards the point of the incision 812. In the illustrated example, the end effector 106 (which remains coupled to the tendon 800) can remain within the incision 812 and manipulated such that the second end 107b (shown in FIG. 3B) thereof is positioned to be the leading end and the first end 107a thereof is positioned to be the trailing end, as shown in FIG. 3B. However, the end effector 106 can also be retracted from the incision 812 and then manipulated such that the second end 107b is positioned to be the leading end. The free first end 800a of the tendon 800 can be withdrawn from the incision 812, as shown in FIG. 8D.

With its second end 107b positioned to be the leading end (as shown in FIG. 3B), the end effector 106 coupled to the tendon 800 is advanced along the tendon 800 in an opposite direction, from the location near the incision 812 towards the opposite, second end 800b of the tendon, as shown in FIG. 8E. The second end 107b of the end effector 106 is used to strip and cut the tendon 800 at the second end 800b thereof. The tendon 800 is thus stripped off of the tibia 808 and is removed in its entirety via the incision 812 for subsequent processing as a graft. Thus, FIG. 8F illustrates the harvested tendon 800 separately from the knee 802. The incision 812 can then be closed using any suitable technique. Alternatively, another tendon can be harvested via the incision 812. For example, if the tendon 800 harvested first is one of the gracilis and semitendinosus tendons, another of the gracilis and semitendinosus tendons can then be harvested. The configuration of the end effector 106 allows advancing it in a manner that decreases or eliminates a possibility of the end effector 106 being diverted from the main tendon 800.

It should be also appreciated that although the illustrated embodiments provide instruments and methods for harvesting a tendon for subsequent use as a graft in a ligament reconstruction surgery involving fixation of anterior or posterior cruciate ligaments, the techniques can be adapted for harvesting other types of tendons and for other surgical procedures as well. For example, the described techniques can be used for harvesting other anatomical structures, such as, for example, nerves and veins.

Having thus described some examples of the described embodiments, various alterations, modifications, and improvements will readily occur to those skilled in the art. Such alterations, modifications, and improvements are intended to be within the spirit and scope of the described embodiments. Accordingly, the foregoing description is by way of example only, and not intended to be limiting.

What is claimed is:

1. A surgical instrument, comprising:
   an end effector mounted on an elongate shaft, the end effector defining a tissue passage configured to separate and receive a length of tissue, the tissue passage having a predefined and static shape; and
   a cutting element,
   wherein the end effector is pivotally mounted to the elongate shaft such that the end effector is configured to be rotatably manipulated during a procedure between a first position and a second position;
   wherein the tissue passage defines a longitudinal axis that is substantially parallel to the elongate shaft in both the first position and the second position; and
   wherein a first terminal end of the end effector is selectively positionable to be one of a leading end and a trailing end, wherein the leading end is distal a distal end of the elongate shaft and the trailing end is proximal the distal end of the elongate shaft.

2. The surgical instrument of claim 1, wherein the cutting element is configured to cut the length of tissue received in the tissue passage.

3. The surgical instrument of claim 1, wherein the end effector includes a first arcuate member and a second arcuate member.

4. The surgical instrument of claim 3, wherein the cutting element is a sharpened edge of at least one of the first and second arcuate members.

5. The surgical instrument of claim 1, wherein the cutting element is a sharpened protrusion extending from the end effector and along an axis defined by the tissue passage.

6. The surgical instrument of claim 1, wherein the cutting element is configured to cut tissue transverse to the longitudinal axis.

7. A surgical instrument, comprising:
   a tissue harvesting guide pivotally mounted on an elongate shaft, the tissue harvesting guide configured to separate and receive a length of tissue, and configured to selectively pivot over about a 180 degree range of motion between a first position proximate a first side of the elongate shaft and a second position proximate an opposed second side of the elongate shaft,
   wherein a first terminal end of the tissue harvesting guide is a leading end of the tissue harvesting guide when the first terminal end is in the first position and wherein the first terminal end of the tissue harvesting guide is a trailing end of the tissue harvesting guide when the first terminal end is in the second position, and
   wherein the leading end is distal to a distal end of the elongate shaft and wherein the trailing end is proximal to the distal end of the elongate shaft.

8. The surgical instrument of claim 7 further comprising a cutting element.

9. The surgical instrument of claim 8, wherein the tissue harvesting guide includes a first extension and a second extension, wherein the first and second extensions define a tissue passage therebetween.

10. The surgical instrument of claim 9, wherein the cutting element is a sharpened edge of at least one of the first and second extensions.

11. The surgical instrument of claim 8, wherein the tissue harvesting guide defines a longitudinal axis and the cutting element is configured to cut tissue in a direction transverse to the longitudinal axis.

* * * * *